United States Patent [19]

Lambert et al.

[11] Patent Number: 5,035,704
[45] Date of Patent: Jul. 30, 1991

[54] BLOOD SAMPLING MECHANISM

[76] Inventors: Robert D. Lambert, 110 North St., Larwill, Ind. 46746; Edward W. Eves, III, 8708 Cobblestone Pl., Fort Wayne, Ind. 46904; Norbert L. Wyss, 4902 Stratford Rd., Fort Wayne, Ind. 46807

[21] Appl. No.: 320,251

[22] Filed: Mar. 7, 1989

[51] Int. Cl.$^5$ .............................................. A61B 17/32
[52] U.S. Cl. ..................................... 606/182; 128/771
[58] Field of Search ............... 128/760, 762, 765, 767, 128/771; 604/51, 192–198, 201; 606/181, 182, 185; 206/569, 571

[56] References Cited

U.S. PATENT DOCUMENTS

| | | | |
|---|---|---|---|
| 2,880,725 | 4/1959 | Kendall | 604/201 |
| 3,741,197 | 6/1973 | Sanz et al. | 606/182 |
| 4,360,016 | 11/1982 | Sarrive | 606/182 |
| 4,469,110 | 9/1984 | Slama | 606/182 |
| 4,637,403 | 1/1987 | Garcia et al. | 606/182 |
| 4,648,408 | 3/1987 | Hutcheson et al. | 128/771 |
| 4,883,068 | 11/1989 | Dechow | 128/760 |

FOREIGN PATENT DOCUMENTS 8504089 9/1985 World Int. Prop. O. .......... 128/767

Primary Examiner—Max Hindenburg
Attorney, Agent, or Firm—Diller, Ramik & Wight

[57] ABSTRACT

A blood sampling mechanism including a housing in which is inserted a magazine containing a plurality of test pads from which individual test pads are sequentially fed to a loading/testing station, each novel test pad being relatively thin and carrying a resilient dermis-piercing member having a pointed end directed toward a slit of a wicking membrane contiguous an exterior test strip, a transfer mechanism for transferring each test pad from the loading/testing station to a blood sampling station, a hammer at the blood sampling station for deflecting the dermis-piercing member with sufficient force to drive the pointed end through the slit and into the dermis causing blood to be wicked through the wicking membrane and into the test strip, the transfer mechanism subsequently transferring the test pad back to the loading/testing station, and optical or equivalent test systems at the loading/testing station for determining constituents of the blood sample.

70 Claims, 4 Drawing Sheets

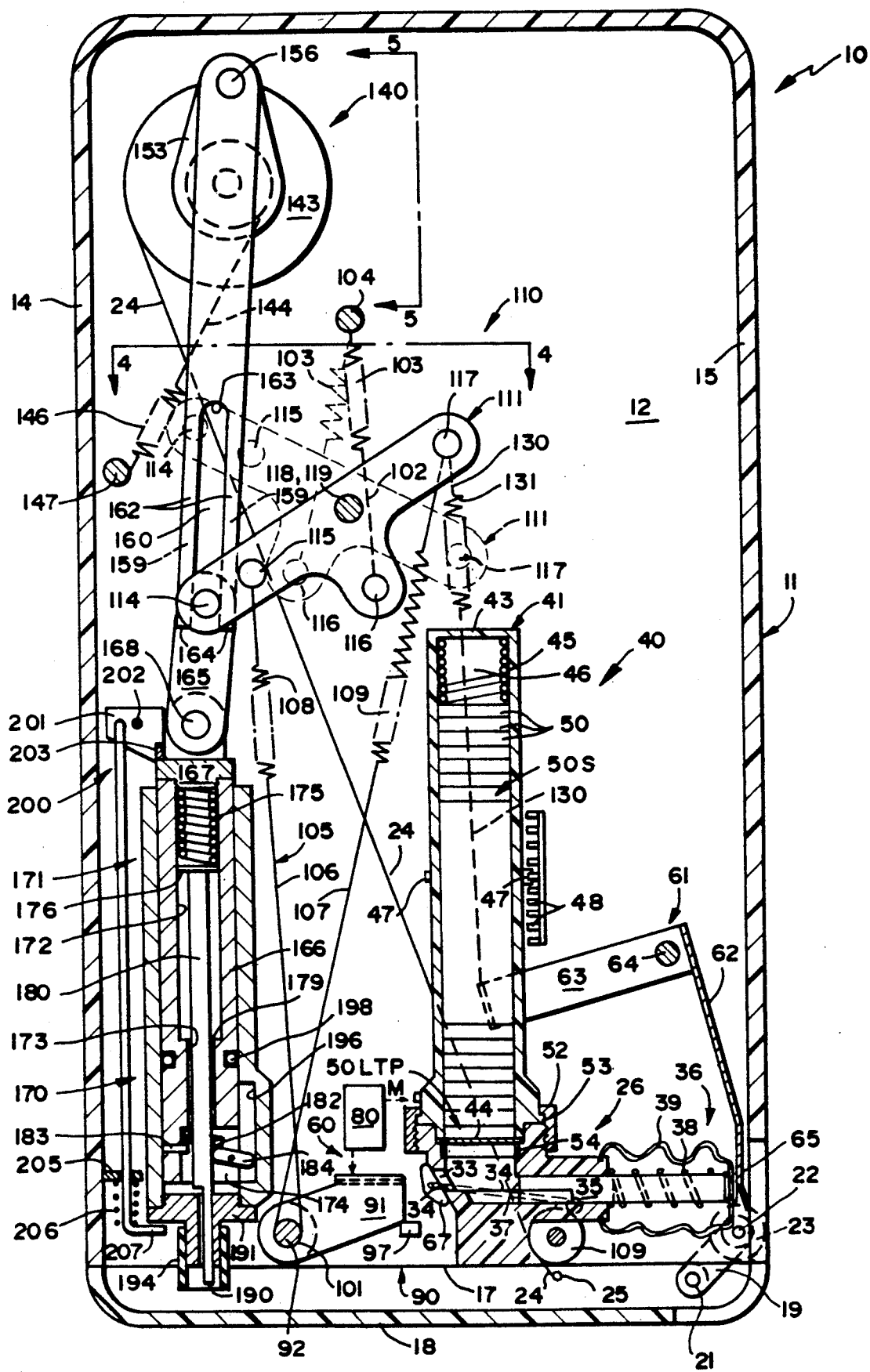
FIG._1

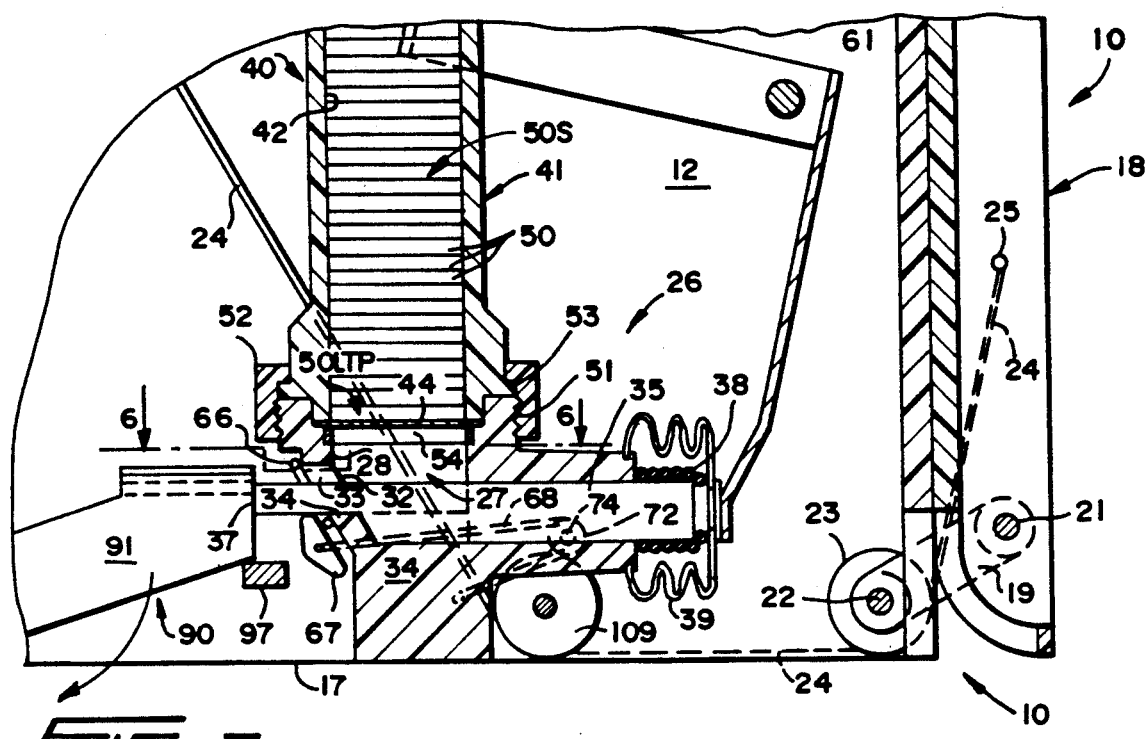

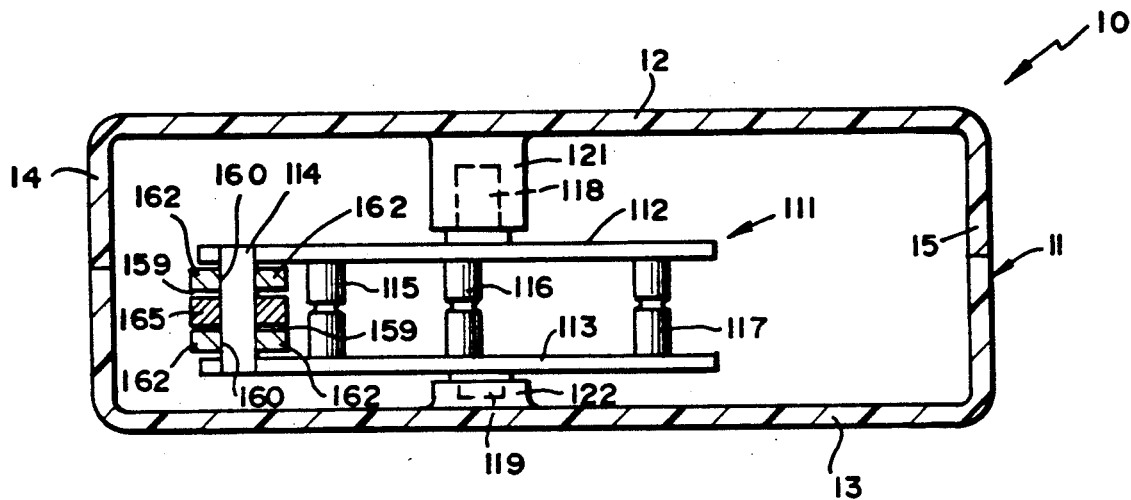
FIG_4
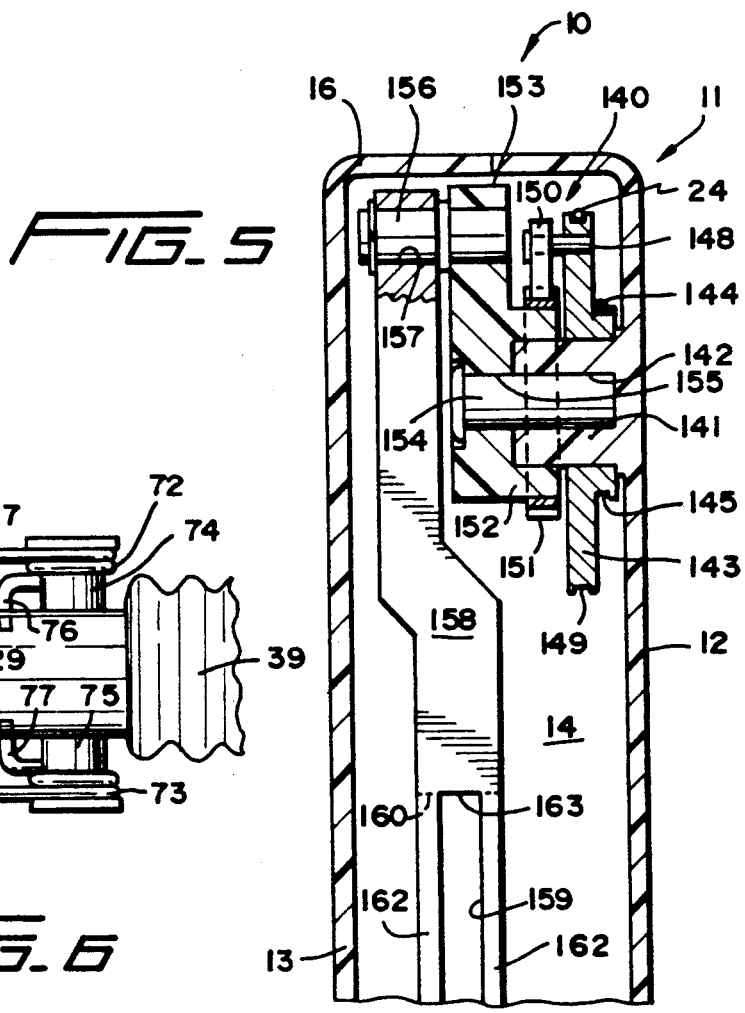
FIG_5
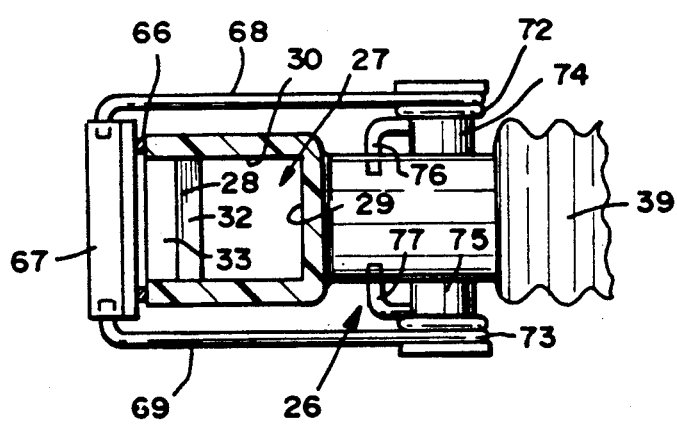
FIG_6

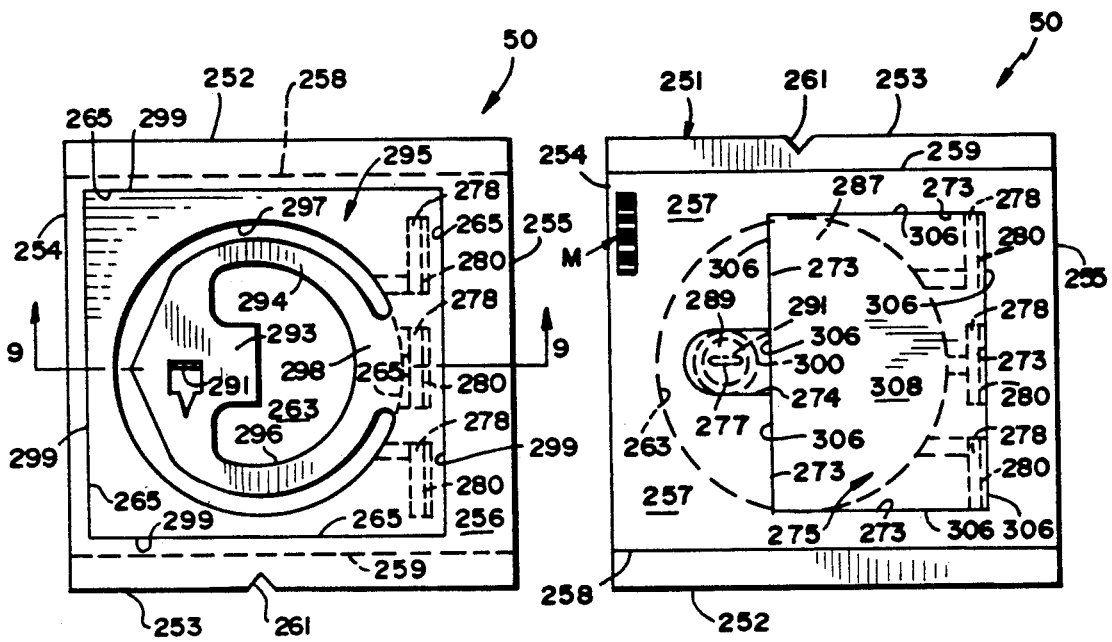
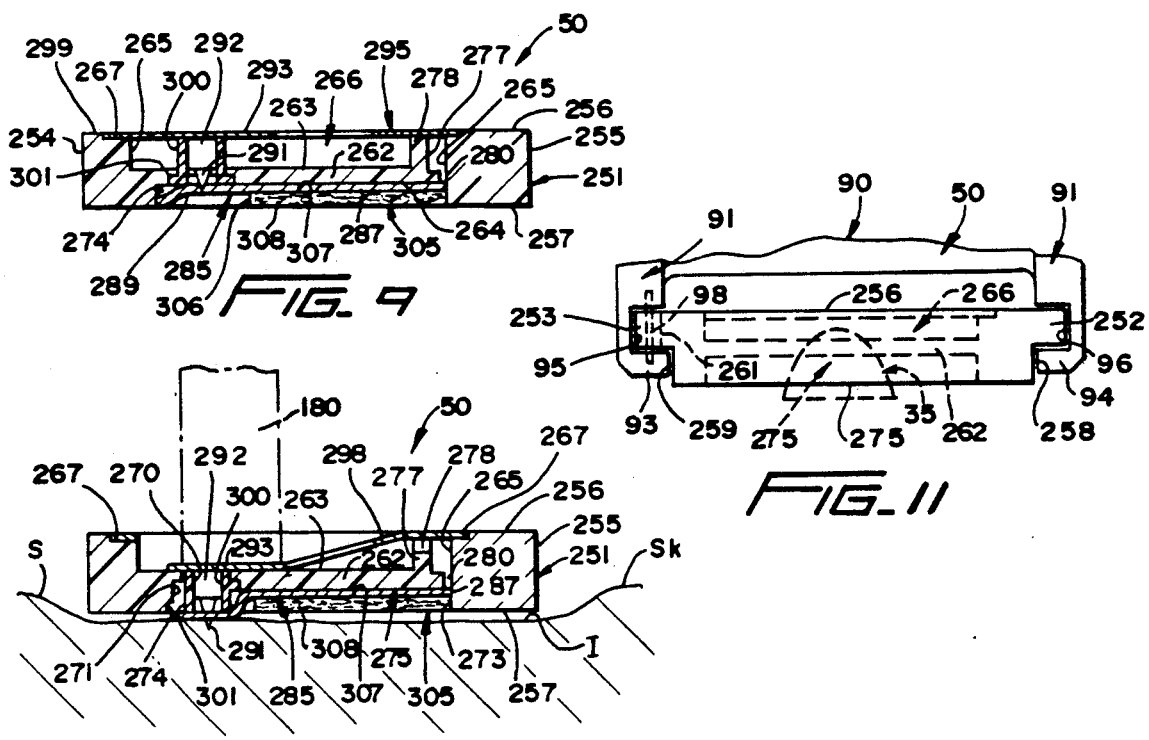

BLOOD SAMPLING MECHANISM

CROSS-REFERENCE TO RELATED APPLICATIONS

The blood sampling mechanism of the present invention utilizes a test strip which is preferably constructed in accordance with pending application Ser. No. 06/896,418 filed Aug. 13, 1986 in the name of Roger Phillips et al., entitled Minimum Procedure System for the Determination of Analytes, and now U.S. Pat. No. 4,935,346.

BACKGROUND OF THE INVENTION

The field of art to which the invention pertains is medical diagnostic mechanisms for measuring blood glucose, urea nitrogen, hemoglobin and other blood components.

DESCRIPTION OF THE RELATED ART

U.S. Pat. Nos. 4,627,445 and 4,637,403 issued Dec. 9, 1986 and Jan. 20, 1987, respectively, in the names of Fernando S. Garcia et al. and entitled Glucose Medical Monitoring System disclose a portable medical diagnostic mechanism for checking measurement of blood glucose, urea nitrogen, hemoglobin, blood components or other body qualities. The system includes a disposable needle package which carries a chemical reagent strip, such as blood reacting chemistry. A needle of the disposable needle package penetrates the skin and a vacuum is created to transfer blood to the chemical reagent strip. Appropriate photosensing circuitry and a microcomputer measures the change of color of the blood reacting chemistry of the reagent strip.

Other related art known to Applicants include U.S. Pat. No. 4,257,427 issued Mar. 24, 1981 to Louis Bucallo entitled Method for Collecting Body Fluids; U.S. Pat. No. 2,940,448 issued June 14, 1960 to Norman B. Furlong, Jr. entitled Disposable Blood-Gas Analyzer; U.S. Pat. No. 4,469,110 issued Sept. 4, 1984 to Gerard J. Slama entitled Device for Causing a Pin Prick to Obtain and to Test a Drop of Blood; and U.S. Pat. No. 4,301,412 issued Nov. 17, 1981 to Jeremy R. Hill et al. entitled Liquid Conductivity Measuring System and Sample Cards Therefor.

SUMMARY OF THE INVENTION

The blood sampling mechanism of the invention includes a housing in which is inserted a magazine containing a plurality of test pads from which individual test pads are sequentially fed to a loading/testing station, transferred to a blood sampling station and returned to the loading/testing station for testing. Each test pad is relatively thin and carries a resilient dermis piercing member having a pointed end directed toward a wicking membrane in contiguous spanning relationship to the pointed end. The wicking membrane contacts a test strip of the type described in the latter-noted application. When the test pad is at the blood test station, a hammer deflects the dermis piercing member with a sufficient force to drive the pointed end through a slit of the wicking membrane and into the dermis causing blood to be "wicked" through the wicking membrane and into the test strip which is subsequently analyzed at the loading/testing station.

The blood sampling mechanism thus briefly described reduces pain, infection and test strip contamination. Moreover, no accessories of any type are required and the skill of the operator/user can be minimal.

In keeping with the foregoing, a novel blood sampling mechanism is provided which is loaded with a magazine containing a plurality of test pads (fifty, for example), and individual test pads are sequentially fed from the magazine to a pivotally mounted transfer arm at a test pad loading/blood testing station. Each test pad carries a resilient dermis piercing member having a pointed end and a slit or rupturable wicking membrane in contiguous spanning relationship to the pointed end. The wicking membrane is sandwiched between a wall of the test pad and a test strip containing blood reacting chemistry. The transfer arm is pivoted to move the test pad to a blood sampling station at which a piston creates a vacuum on the test pad while a hammer impacts against the dermis piercing member to drive the pointed end through the rupturable wicking membrane or the slit thereof and into the dermis creating blood flow via the wicking membrane to the test strip. The arm then returns the test strip to the test station for appropriate blood constitute testing.

The blood sampling mechanism thus specifically described reduces pain by avoiding the utilization of a lance or needle which can penetrate the dermis as much as 0.250 inch. Instead the pointed end of the dermis piercing member of the present invention controllably penetrates the epidermis approximately 0.007 inch which is sufficient to expose the blood rich dermis, yet is less painful. Also, the hammer impacts the dermis-piercing member into the skin at an extremely high velocity to minimize the pain of entry. Psychological pain is also eliminated since the pointed end is hidden and unobtrusive at all times, including prior to, during and after the entire operating sequence of the blood sampling mechanism, and the ofttimes psychologically disturbing appearance of a lance or needle is totally eliminated. Furthermore, any foreign matter on the skin will not be carried so deep into the skin that the outflow of blood will not remove the same thereby assuring the absence of infection.

Apart from loading the magazine into the blood sampling mechanism, the entire operation is essentially automatic and manual manipulation of the test pad is unnecessary. This assures that the "active" surface of the blood reactive test strip will not be exposed to a person's fingers and attendant contact, rubbing, drying and/or foreign matter deposition, all of which are capable of changing the response to subsequent blood sample testing.

Another advantage of the blood sampling mechanism is the repetitive minimal depth of penetration of the pointed end due to the relatively short length thereof, as well as the repetitive nonvariable force applied by the hammer to the dermis piercing member carrying the pointed end.

Finally, since the blood sampling mechanism operates relatively automatically, except for initial "loading" and "arming," even inexperienced operators can assure reliable results by following the simplest of instructions.

With the above and other objects in view that will hereinafter appear, the nature of the invention will be more clearly understood by reference to the following detailed description, the appended claims and the several views illustrated in the accompanying drawings.

BRIEF DESCRIPTION OF THE DRAWINGS

FIG. 1 is a longitudinal sectional view through a novel blood sampling mechanism of the present invention, and illustrates a sealed and desiccated magazine containing a plurality of test pads, a test pad feed mechanism for sequentially bottom-feeding individual test pad to a pivotally mounted transfer arm at a test pad loading/blood testing station, and a vacuum-producing piston mechanism including a hammer for imparting a force to a dermis piercing member to drive its associated pointed end into the dermis effecting blood sampling at a blood sampling station.

FIG. 2 is an enlarged fragmentary sectional view of the magazine, feeder mechanism and transfer arm, and illustrates a plunger at the end of its test pad feed stroke.

FIG. 3 is an enlarged fragmentary sectional view of the piston mechanism of FIG. 1, and illustrates the test pad position at the blood sampling station and the piston and hammer prior to the operation being triggered by pressing the meter against the skin.

FIG. 4 is a cross-sectional view taken generally along line 4—4 of FIG. 1, and illustrates the details of a pivoted bell-crank lever forming part of an "arming" system of the blood sampling mechanism.

FIG. 5 is a cross-sectional view taken generally along line 5—5 of FIG. 1, and illustrates details of a clutch, crank and crank arm of the arming system.

FIG. 6 is a cross-sectional view taken generally along line 6—6 of FIG. 2, and illustrates a test pad feed chamber, an opening and a door normally closing the opening.

FIG. 7 is a top plan view of test pad of the present invention, and illustrates a body carrying a resilient dermis piercing member having a depending pointed end.

FIG. 8 is a bottom plan view of the test pad of FIG. 7, and illustrates a portion of the slit wicking membrane and the active surface of a chemical reagent test strip.

FIG. 9 is a cross-sectional view taken generally along line 9—9 of FIG. 7, and illustrates the relationship of the piercing member pointed end, the wicking membrane and the test strip prior to the deflection of the resilient dermis piercing member incident to obtaining a blood sample.

FIG. 10 is a cross-sectional view of the test pad also taken generally along line 9—9 of FIG. 7, and illustrates a hammer of the piston mechanism in phantom outline deflecting the dermis piercing member to cause the pointed end to pass through the wicking membrane and pierce the dermis.

FIG. 11 is an end elevational view taken generally along line 11—11 of FIG. 3, and illustrates the test pad being gripped between opposing grooves of the pivotally mounted transfer arm.

DESCRIPTION OF THE PREFERRED EMBODIMENT

A novel blood sampling mechanism constructed in accordance with this invention is generally designated by the reference numeral 10 (FIG. 1), and includes a housing 11 defined by generally parallel side walls 12, 13 (FIG. 4), generally parallel end walls 14, 15 (FIG. 4) and a top wall 16 (FIG. 5). The walls 12 through 15 collectively define a bottom peripheral edge 17 (FIGS. 1-3) which is normally closed by a relatively shallow cup-shaped door 18 (FIG. 1) which can be pivoted to an open position (FIG. 2) through a pivoted connection which includes a pin 21 spanning and connected to opposite walls (unnumbered) of the door 18, another pin 22 spanning and connected between the side walls 12, 13, and a link 19 connected to the pins 21, 22 and pivoted relative thereto between the open (FIG. 2) and closed (FIG. 1) positions thereof. The pin 22 carries a peripherally grooved roller 23 which cooperates with a cable 24 connected at one end to a pin 25 (FIG. 1) fastened to one of the walls (unnumbered) of the door 18 for the purpose of "arming" or "loading" the blood sampling mechanism 10 incident to the operation thereof, as will be described more fully hereinafter.

A test pad magazine support 26 is rigidly connected between the side walls 12, 13 adjacent the door 18 (FIG. 1) and includes a relatively polygonal or square test pad receiving and feeding chamber 27 (FIGS. 1, 2 and 6). The chamber 27 is defined by opposite parallel walls 28, 29 (FIG. 6) and another opposite pair of parallel walls 30, 31. A wall 32 converges downwardly from its intersection with the wall 28 (FIG. 2), and has a rectangular opening 33 formed therein. A lower edge 34 (FIG. 2) of the opening 33 also defines a lower generally horizontal support surface upon which will eventually rest a lowermost test pad 50 LTP of a stack of test pads 50S housed in a magazine 40 when a test pad feed plunger 35 of a test pad feed mechanism 36 is in the retracted or "home" position of FIG. 1. The test pad feed plunger 35 has an end 37 (FIG. 1) which engages the lowermost test pad 50 LTP and each subsequent test pad 50 resting upon the surface 34 to feed each successive test pad 50 outwardly of the test pad receiving and feeding chamber 27 to a test pad loading and blood sampling station 60 to be described more fully hereinafter.

The magazine 40 includes tubular body 41 defining an interior chamber 42 closed by an end wall 43 at one end and by a frangible seal 44 at an opposite end thereof. Approximately fifty of the test pads 50 form the stack 50S and a spring 45 encircling desiccant 46 normally urges the test pad stack 50S downwardly to cause sequential downward feeding thereof as each bottommost or lower test pad 50 LTP is fed from right-to-left by the successive reciprocation of the test feed plunger 35. The seal 44 can be removed prior to assembling the magazine 40 upon the test pad feed mechanism 36 through a conventional threaded stem 51 of the test pad magazine support 26 to which is threaded a threaded nut or collar 52 having a flange (unnumbered) which engages a flange 53 of the magazine 40. If the seal 44 is not manually removed from the lowermost test pad 50 LTP, a knife 54 having a rectangular profile corresponding to the exterior profile configuration and dimension of the test pads 50 severs or shears the seal 44 under the downward force of the nut 53 as it brings the magazine flange 53 into engagement with the threaded stem 51. The lowermost test pad 50 LTP thus carries a portion of the seal 44 to the test pad loading and blood testing station 60. Unavoidable variations in test pad production require that each magazine 40 be provided with a code number of the production batch from which it is filled and that the meter electronics be adjusted/calibrated to accord with the code number of the magazine being used. Such a code can be in the form of an exterior circumferential band or knob 47 which is applied to the body 41 of the magazine 40 at a specific axial location along the length thereof which position is reflective of the particular production batch from which the magazine 40 is filled. The magazine 40 is inserted through a sliding panel (not shown) in the back of the housing 11 and is guided by guide bars (not shown) to a position at which it can be attached in the manner shown in FIG. 1. When so attached, the knob 47 will actuate one micro switch of a set of axially spaced micro switches 48, and the meter electronics will thus be calibrated/adjusted. There are ten micro switches 48 shown in FIG. 1, and these can be suitably mounted in a fixed position relative to each magazine 41 mounted in the housing 11. Thus, if one of the knobs 47 is positioned on the magazine body 41 above or below the position shown in FIG. 1, different single ones of the micro switches 48 will be actuated. Thus, a single one of the knobs 47 specifically located in one of ten possible relative positions along the body 41 of the magazine 40 will actuate one of the ten micro switches 48 to effect the calibration heretofore noted. Alternately, the lowermost test pad 50 LTP may be a calibrated test pad which is sensed by conventional calibrating, blood testing and discriminating means 80 of the type set forth in the latter-noted patents which calibrate the blood sampling mechanism 10 for subsequent blood sample testing. However, in the case where the lowermost test pad 50 LTP carries the severed portion of the seal 44 therewith to the loading station 60, this test pad is cycled through one cycle of the blood sampling mechanism operation and discharged without being used to draw or test a blood sample, as will be described more fully hereinafter.

The test pad feed mechanism 36 includes a compression spring 38 which normally urges the plunger 35 to its retracted position (FIG. 1), and the spring 38 and a portion (unnumbered) of the plunger 35 projecting out of the test pad magazine support 26 are both covered by a flexible cover 39. A feed lever 61 of the test pad feed mechanism 36 includes a pair of arms 62, 63, the latter of which is mounted for rotation about a pin 64 spanning and engaged to the side walls 12, 13. A terminal end 65 of the arm 62 normally rests against the end (unnumbered) of the feed plunger 35. Upon clockwise pivoting of the feed lever 61 from the position shown in FIG. 1 to the position shown in FIG. 2, the test pad feed plunger 35 is shifted to the left compressing the spring 38 and feeding the lowermost of the test pads 50 LTP from the test pad stack 50S through the opening 33 and to the loading and testing station 60. The manner of pivoting the feed lever 61 will be described hereinafter, but it is to be noted that opposite pivoting of the lever 61 in a counterclockwise direction is effected under the influence of the compressed spring 38 (FIG. 2).

The opening 33 of the test pad feed mechanism 36 is surrounded by a seal 66 (FIG. 6) against which rests a door 67 pivotally connected to spring arms 68, 69 (FIG. 6) having respective coil portions 72, 73 coiled about axially aligned oppositely directed projections 74, 75 of the test pad magazine support 26. Terminal ends 76, 77 of the arms 68, 69, respectively, are received in blind bores (unnumbered in FIG. 6) of the test pad magazine support 26. As each test pad 50 is fed by the test pad feed plunger 35 outwardly through the opening 33 (FIG. 2), the test pad 50 pivots the door 67 counterclockwise, as viewed in FIGS. 1 and 2, and deflects the spring arms 68, 69 downwardly in a counterclockwise direction as viewed in FIG. 2 relative to the projections 74, 75, thus tensioning the coil portions 72, 73 which automatically return the arms 68, 69 and the associated door 67 from the open position (FIG. 2) to the closed position (FIG. 1) upon the retraction of the test pad feed plunger 35 to the position shown in FIG. 1.

Means generally designated by the reference numeral 90 are provided for conveying each test pad from the test pad loading and testing station 60 to a blood sampling station 100 (FIG. 3). The means 90 includes a conveyor or transfer arm 91 having an end fixed to a rod 92 (FIGS. 1 and 3) conventionally mounted for rotation between the side walls 12, 13. An opposite end of the arm 91 is bifurcated to define a pair of arm ends 93, 94 having respective slots or grooves 95, 96 (FIG. 11) in opposing relationship to each other. The slot or groove 95 is spanned by a spring 98 which is be temporarily deflected when one of the test pads 50 (FIG. 11) is fed into the grooves 95, 96 by the test pad feed plunger 35, as will be described more fully hereinafter. The arm 91 is rotated from the position shown in FIG. 1 to the position shown in FIG. 3 and returned to the FIG. 1 position by movement imparting "arming" means 110 (FIG. 1) which includes a bell-crank lever 111 (FIGS. 1 and 4) formed by a pair of arms 112, 113 (FIG. 4) connected together and carrying four pins 114 through 117. Projections 118, 119 (FIG. 4) are in axial alignment, project from the respective arms 112, 113 and are mounted for rotation in respective bosses 121, 122 of the respective side walls 12, 13. A cable 105 (FIG. 1) includes cable portions 106, 107 having a crossing bight cable portion 101 partially entrained about the rod 92. The cable portions 106, 107 include respective springs 108, 109 and respective ends of the latter are connected to the respective pins 115, 117.

The bell crank lever 111 is connected to a piston 166 by a link 165 in the manner which will be more fully described hereinafter. However, it should be noted that the bell crank lever 111 is shown in solid position in FIG. 1 with the piston 166 down, springs 109 and 131 extended to create forces on cables 107 and 130, respectively, while spring 108 is shortened to reduce forces on cable 105, and a spring 103 with cable 102 having moved over center of pivots 118, 119 creates a counterclockwise force on the bell crank lever 111. The resultant of all of these forces is an upward force on the pin 114, link 165, pin 168 and, hence, on pin 166, as well as an upward force on cable 130. Spring 103 and cable 102 act to balance forces on pivot 118, 119 and to maintain a generally uniform upward force on the piston 166 throughout its stroke (See FIG. 12).

A cable 130 (FIG. 1) having a spring 131 is also connected at one end to the pin 117 and at its opposite end to the arm 63 of the feed lever 61. When the bell-crank lever 111 is moved counterclockwise from the phantom outline position of FIG. 1 to the solid outline position by opening door 18, an upwardly directed force on the cable 130 pivots the feed lever 61 clockwise about the pivot pin 64 to move the feed plunger 35 from right-to-left, as viewed in FIG. 1, to effect the bottom feeding of the lowermost test pad 50 LTP, as was heretofore noted. Opposite clockwise rotation of the bell crank lever 111 from the solid to the phantom outline position of FIG. 1, actuated when the piston 166 is triggered to move upward, reduces the effective upward force of the spring 131 and the compressed compression spring 38 (FIG. 2) overcomes the force of the spring 131 to return the feed lever 61 from the position shown in FIG. 2 to the position shown in FIG. 1 by counterclockwise pivoting of feed lever 61 about the pin 64.

The movement imparting and arming means 110 also includes a clutch and crank assembly means or mechanism 140 (FIGS. 1 and 5) which is mounted on a cylindrical boss 141 (FIG. 5) projecting away from the side wall 12 and having a cylindrical blind bore 142. A drum 143 includes a groove 149 in its periphery (unnumbered) which partially entrains therein and thereabout the cable 24 which, as earlier described, is also connected to the pin 25 (FIG. 1) of the door 18. Another cable 144 is fixed to the drum 143 and is partially wound in another peripheral groove 145 thereof. A spring 146 of the cable 144 is connected to a pin 147 fixed between the side wall 12. The drum 143 is freely rotatable upon the boss 141 and carries a pin 148 (FIG. 5) which in turn carries a ratchet or dog 150. The ratchet or dog 150 engages in teeth (unnumbered) of a ratchet wheel 151 carried by a cylindrical boss 152 of a crank arm 153 which is mounted for rotation on the boss 141 by a pivot pin 154 which passes through a bore 155 in the crank arm 153 and is threaded or otherwise fixed in the blind bore 142. A pin 156 is fixed to the crank arm 153 and pivotally mounted thereto by a bore 157 is a cam arm 158 having slots 159, 160 crossing each other at 90 degrees (FIG. 4). The slot 160 slidingly receives the pin 114 (FIG. 4) of the bell-crank lever 111. The crossing slots 159, 160 define four legs 162 of the cam arm 158 which extend from a blind end 163 of the slot 160 to a lower free end 164 of each leg 162. The pin 114 of the bell-crank lever 111 rides in the slots 160 and is also pivotally connected to a link 165 pivoted by a pin 168 to an end cap 167 of a piston 166 forming part of a blood sampling means or mechanism 170 (FIGS. 1 and 3).

The blood sampling means or mechanism 170 includes an exterior cylinder or housing 171 which is suitably fixed to and between the side walls 12, 13. The piston 166 is mounted for reciprocal movement in the cylinder 171. The piston 166 includes a bore 172 having an annular surface 179 and a counterbore 173 opening at its lower end in a radially opening slot 174 (FIG. 3). A spring 175 is housed in the bore 172 between a head 176 of a hammer 180, having a shoulder 189, and the end cap 167. The spring 175 normally biases the hammer 180 downwardly, but the hammer 180 is selectively locked in the retracted position shown in FIGS. 1 and 3 by a locking ring 182 which has one diametrical side supported by the free end (unnumbered) of an axial pin 183 (FIG. 3) carried by the piston 166 and an opposite diametric side contacted and moved in a selective fashion by a cam 184 pivotally mounted by a pin 185 spanning the radially opening slot 174 in the piston 166. The locking 182 is illustrated in its canted locking position relative to the hammer 180 in FIGS. 1 and 3, but when the locking ring 182 is moved by the cam 184 to a horizontal uncanted position through the operation of the cam 184, the hammer 180 is unlocked or released and the force of the spring 175 drives the hammer 180 downwardly with the result that an end 190 of the hammer 180 cooperates with each of the test pads 50 to effect the blood sampling at the blood sampling station 100, as will be described more fully hereinafter.

The cylinder 171 carries an end cap 191 at its lower end which in turn includes a tubular projection 192 defining a bore 193 through which the hammer end 190 projects. A soft rubber sleeve 194 surrounds the tubular projection 192, and a lower edge (unnumbered) thereof seals against the test pad 50 (FIG. 3) when the meter peripheral edge 17 (FIG. 1) and, hence, the exposed test pad 50 is placed forcefully against an upper surface S of a person's skin Sk from which a sample of blood is to be drawn. The purpose of the tubular sleeve 194 is to encircle an area above the test pad 50 (FIG. 3) which is subject to negative pressure or vacuum upon operation of the blood sampling means 170 as the piston 166 moves upwardly generally simultaneously with the downward movement of the hammer 180 under the influence of the compression spring 175. The latter relative motion, which will be described more fully hereinafter, creates a vacuum defined in the volume set-off by the sleeve 194, the bore 193, the radially opening slot 174, the counterbore 173, the bore 172 and an elongated slot 196 in the cylinder 171 in which rides an end (unnumbered) of the cam 184. An opposite end (unnumbered) of the cam 184 engages the underside of the lock ring 182 diametrically opposite the pin 183 (FIG. 3). A O-ring 198 carried by the piston 166 prevents leakage between the piston 166 and an interior surface (unnumbered) of the cylinder 171 during evacuation. An edge 197 (FIG. 3) of the slot 196 moves the cam 184 from the position shown in FIG. 1 to the phantom outline position shown in FIG. 3 to effect the unlocking of the locking ring 182 as the piston 166 moves upwardly, as will be described hereinafter.

The mechanism 170 is illustrated in FIG. 1 in its armed and locked position, and the mechanism 170 is retained in this position by a locking and triggering means or mechanism 200 which includes a trigger 201 pivotally connected by a pivot pin 202 fixed between the side walls 12, 13. A nose 203 of the trigger 201 rests atop the end cap 167 in the armed condition illustrated in FIG. 1. A triggering rod 204 is pivotally connected to the trigger 201 and is mounted for vertical reciprocal guiding movement in a bore (unnumbered) of a projection 205 projecting inwardly from the side wall 14. A spring 206 is housed between the underside of the projection 205 and an inward projecting end 207 of the trigger rod 204. The spring 206 normally pulls the trigger rod 204 downwardly which draws the trigger 201 in a counterclockwise direction about the pivot pin 202 to maintain the nose 203 in overlying relationship to the end cap 167 of the piston 166. However, when the arm 91 is pivoted to the position shown in FIG. 3, but before the test pad 50 is pushed against the surface S of the skin Sk, a trigger abutment bar 97 fixed to the arm 91 contacts the underside of the end 207 of the trigger rod 204. In this position the trigger rod 204 remains stationary but as the test pad 50 carried by the arm 91 is pushed against the surface S of the skin Sk, the rubber sleeve 194 compresses and yields which causes the arm 91 to pivot slightly clockwise about the rod 92, as viewed in FIG. 3, whereupon the trigger abutment bar 97 pushes the end 207 upwardly, as shown in phantom outline in FIG. 3, against the force of the spring 206 causing the trigger rod 204 to move upwardly which in turn pivots the trigger 201 clockwise about the pivot pin 202 to release the nose 203 which in turn permits the piston 166 to move upwardly by the spring-actuated clockwise pivoting of the bell-crank lever 111. It is this upward movement of the piston 166 which creates the vacuum or negative pressure heretofore noted and subsequent thereto as the piston 166 continues its upward movement, the right-hand edge of the cam 184 contacts the edge 197 of the slot 196 of the cylinder 171 which rotates the cam 184 clockwise causing the left-hand of the cam 184 to cant the locking ring 182 to its unlocked position. When the locking ring 182 unlocks, the spring 175 drives the hammer 180 downwardly effecting blood sampling in conjunction with the associated test pad 50.

The test pad 50 is illustrated in FIGS. 7 through 9 of the drawings and includes a test pad body or frame 251 of a generally polygonal or square configuration (FIGS.

7 and 8) having opposite generally parallel side edges of faces 252, 253, opposite generally parallel end edges of faces 254, 255, an upper relatively flat planar surface 256 (FIGS. 7 and 9) and a relatively planar lower surface 257. The surfaces 256, 257 (FIG. 9) are in generally parallel relationship to each other and are relatively closely spaced thereby imparting a relatively thin, flat, planar configuration to the overall test pad 50. The side edges 252, 253 also have respected notches 258, 259 (FIGS. 7, 8 and 11) which impart a thickness to the side edges 252, 253 slightly less than the size of the respective grooves 95, 96 respectively (FIG. 11), of the transfer arm 91 which facilitates the introduction of the side edges 252, 253 into the respective grooves 96, 95 by the test pad feed plunger 35 (FIG. 2).

The test pads 50 are stacked in the magazine 40 with the surfaces 257 uppermost, the end edges 254 remote from the end 37 of the test pad feed plunger 35 and the end edges 255 immediately adjacent the end of the feed plunger 35. Therefore, when the feed plunger 35 moves from the position shown in FIG. 1 to the position shown in FIG. 2, the end 37 thereof contacts the end edge 255 to slide the lowermost test pad 50 LTP outwardly of the opening 33 and upon the transfer arm 91 with the side edges 252, 253 received in the respective grooves 96, 95. The spring 97 engages in a V-shaped notch 261 of the side edge 253 to hold each test pad 50 upon the transfer arm 91 during movement between the stations 60, 100.

The body 251 includes a medial wall 262 (FIG. 9) positioned between the surfaces 256, 257 and set-off by an upper circular recessed surface 263 and a lower recessed surface 264. The surface 263 is bounded by a generally circular peripheral wall or surface 265 which defines therewith a generally circular upwardly opening cavity 266. A shallow rectangular recess 299, corresponding generally to the thickness of the dermis-piercing member 295, is stepped in the surface 256 surrounding the circular cavity 266 and it locates and supports the dermis-piercing member 295 without increasing the overall thickness of the test pad 50. A circular bore 270 and a circular counterbore 271 open through the respective surfaces 263, 264 (FIG. 10). The surface 264 also merges with a generally rectangular peripheral edge 273 (FIG. 8) broken along one side by a generally U-shaped edge or cut-out 274 which collectively define a cavity 275. The medial wall 262 includes an axially upwardly directed wall 277 (as viewed in FIG. 9) having three cut-outs 278 and three slots 280 adjacent thereto passing through the surfaces 263, 264. Each cut-out 278 and its associated slot 280 place the cavities 266, 275 in fluid communication with each other at the right-hand side thereof, as viewed in FIG. 9, for a purpose which will be described more fully hereinafter.

Wicking means or a wicking membrane formed of wicking material which will wick blood therethrough is generally designated by the reference numeral 285, and the configuration thereof corresponds generally to the configuration of the walls 273, 274 of the cavity 275 (FIG. 8). Thus, the wicking membrane 285 includes a generally rectangular or polygonal portion 287 and a generally C-shaped portion 289 having a slit 277 (FIG. 8). The C-shaped portion 289 is housed generally in the area bounded by the wall 274 and in opposed spanning relationship to a pointed end 291 of a steel or like dermis-piercing means or member 295. The pointed end 291 is part of a tab 292 struck and bent from the plane of an enlarged area 293 of a generally ring-like portion 294 of the dermis-piercing member 295. The pointed end 291 is aligned with the slit 277 (FIG. 8). The ring-like portion 294 is defined by a centrally located relatively wide inverted C-shaped opening 296 (FIG. 7) and another larger C-shaped opening 297 having ends (unnumbered) defining a hinge area or hinge means 298 which will permit the ring-like portion 294 to deflect and rebound under the inherent resiliency of the material of the dermis-piercing member 295, as will be described more fully hereinafter. The dermis-piercing member 295 is of an overall rectangular configuration, as defined by an outboard rectangular peripheral recess 299 which is seated in and bonded to the stepped edge 267 bounding the peripheral wall 265 of the cavity 266 (FIGS. 7 and 9). The C-shaped portion 289 of the wicking membrane 285 is received in the C-shaped cut-out 274 of the cavity 275 which holds the portion 289 of the wicking member 285 with its slot 277 aligned with the point 291 and against the face 307 of the test pad strip 285 in the area at which the latter will contact the skin S when a blood sample is being obtained, as described more fully hereinafter. The portion 274 of the wicking membrane 285 slopes upwardly and to the right as viewed in FIG. 9, and through the point 291 is within the slot 277, it does not project through the bottom of the portion 289 so that the point can not entrain parts of the wick as it pierces the dermis. Thus, the point 291 will be hidden, as viewed from below in FIG. 9, yet when the point 92 passes through the slot 277, it will not carry with it any part of the wicking material of the wicking membrane 305.

A resilient rubber sleeve 300 surrounds the tab 292 and has an exterior diameter easily movable axially in the bore 270. The sleeve 300 also includes a radially outwardly directed lip 301 which has a diameter easily movable axially in the counter-bore 271.

A generally rectangular test strip 305 is defined by a peripheral edge 306 (FIG. 8) and includes an inactive surface 307 positioned against and adhered to the opposed surface (unnumbered) of the wicking membrane 285. The test strip 305 also includes an "active" surface 308 which is the bottom or exposed surface in FIG. 9. The test strip 305 is preferably constructed in accordance with the test strip of the latter-noted application to effect blood sampling and blood testing, preferably through optical scanning of the active surface 308. Thus, the active surface 308 (FIG. 8) is presented upwardly and the pointed end 291 points upwardly when each test strip 50 is fed upon the transfer arm 91 at the test pad loading and blood sample testing station 60, but upon the rotation of the arm 91 clockwise from the position shown in FIG. 1 to the position shown in FIG. 3, at the blood sampling station 100 the active surface 308 is positioned against the surface S of the skin Sk and the pointed end 291 is pointed downwardly generally normal to the surface S.

A cycle of the blood sampling mechanism 10 will now be described assuming that the bell-crank lever 111 is in its phantom outline position, the trigger 201 is unlatched and accordingly the piston 166 projects upwardly further beyond the cylinder 171 than illustrated in FIG. 1 and the hammer likewise projects downwardly further than that illustrated in FIG. 1 because of the expanded condition of the spring 175. It is also assured that the seal 44 has been manually removed from the lowermost test pad 50 LTP, the latter rests upon the surface 34, and the testing, calibrating and discriminating means 80 has been conveniently calibrated in accordance with the latter-noted Garcia et. al. patents or by suitable scanning calibration codes (not shown) upon the tubular body 41 of the magazine 40 incident to the cycle of operation now to be described.

The door 18 is swung open from the position shown in FIG. 1 to the position shown in FIG. 2 which energizes the means 80 and pulls the cable 24 downwardly along the peripherally grooved guide roller 109 and subsequently along the peripherally grooved roller 23. The downward movement of the cable 24 rotates the drum 143 counterclockwise, as viewed in FIG. 1, which rotates the crank arm 153 through 360 degrees from the 12 o'clock position illustrated back to the same 12 o'clock position at which time the cable 144 is wound upon the peripheral groove 145 of the drum 143 (FIG. 5) causing loading or stretching of the spring 146. During the counterclockwise rotation of the crank arm 153 through the first 180° to the 6 o'clock position, the cam arm 158 moves downwardly and the upper blind end 163 of the slot 160 thereof bears against the pin 114 (FIG. 4) of the bell-crank lever 111 causing the bell-crank lever 111 to pivot about the pivot pins 118, 119 (FIG. 4) from the phantom outline position of FIG. 1 to the solid line position thereof. The downward movement of the cam arm 158 also moves the pin 114 downwardly as the bell-crank lever 111 pivots counterclockwise which pushes the piston 166 downwardly into the cylinder 171 through the link 165 until the trigger 201 can swing counterclockwise about the pivot 202 under the influence of the spring 206 to the position shown in FIG. 1 with the nose 203 in its locked position at the top of the threaded end cap 165. During the initial downward movement of the piston 166 into the cylinder 171, the cam 184 is positioned, as shown in phantom outline in FIG. 3, which holds the locking ring 182 in its unlocked position. The hammer 180 is lower than illustrated in FIG. 1, namely, with the head 176 resting upon the annular surface 179, because of the earlier release of the spring 175. When the link 114 reaches the solid line position shown in FIG. 1, the trigger 201 pivots counterclockwise about the pin 202 under the influence of the spring 206 bringing the nose 203 into overlying locking engagement with the end cap 167.

The same counterclockwise rotation of the bell-crank lever 111 from the phantom outline to the solid line position in FIG. 1 creates an upward force upon the spring 131 and the cable 130 which causes clockwise rotation of the feed lever 61 about the pivot pin 64 with the result that the terminal end 65 of the arm 62 moves the piston 35 from right-to-left against the bias of the spring 38 to feed the lowermost test pad 50 LTP outwardly through the opening 33 and pass the progressively opened door 65 and onto the transfer arm 91, as shown in FIG. 11.

During the same counterclockwise rotation of the bell-crank lever 111 from the phantom outline to the solid line position in FIG. 1, an upward force is generated on the spring 109 and the cable 107 tending to rotate the rod 92 and the transfer arm 91 clockwise. However, the spring 108 creates an oppositely directed force on the cable portion 106 resisting the clockwise pivoting of the transfer arm 91. Also, during the transfer of the test pad 50 by the plunger 35 onto the transfer arm 91, the end face 37 of the plunger 35 eventually abuts against the arm 91, as shown in FIG. 2. Any tendency of the arm 91 to pivot clockwise (FIG. 2) under the influence of the balance forces creating an effective upward force along the cable 107 is resisted by the leftward directed force, as viewed in FIG. 2, as the plunger 35 finally seats the test pad 50 upon the arm 91, and it is only after the latter has occurred that the arm 91 will freely pivot clockwise (FIG. 2). Therefore, during the initial counterclockwise pivoting of the bell-crank lever 111 from the phantom outline position to the solid line position in FIG. 1, the transfer arm 91 does not pivot and remains stationary until the lowermost test pad 50 LTP has been fed thereon. It is only after the bell-crank lever 111 is pivoted counterclockwise sufficiently to transfer the cable 102 from its left-side phantom outline position in FIG. 1 relative to the pivots 118, 119 across dead center and to the right-side solid line position thereof illustrated in FIG. 1 that the additional force of the spring 103 directed upwardly relative to the right-side of the bell crank lever 111 augments the upward force of the spring 109 such that the total force on the cable 107 overcomes the progressively lessening force of the spring 108 as the bell-crank lever rotates counterclockwise to now pivot the transfer arm 91 from the solid position shown in FIG. 1 to the position shown in FIG. 3 at the blood sampling station 100.

During the second 180° of rotation of the crank arm 153 (from 6 o'clock to 12 o'clock counterclockwise in FIG. 1), the slot 160 moves upwardly as it is carried by the cam arm 158 but it is functionless other than to permit the crank arm 153 to return to its 12 o'clock or home position for subsequent cycling.

With the test pad 50 now at the test station 100 (FIG. 3) the blood sampling mechanism 10 is bodily pushed downwardly, as viewed in FIG. 3, against the surface S of the skin Sk which both causes a slight indentation I and additionally compresses the sleeve 194 allowing the transfer arm 91 to pivot slightly clockwise which lifts the trigger abutment bar 97 upwardly against the end 207 of the trigger rod 204 and against the bias of the spring 206 to pivot the trigger 201 clockwise and release the nose 203 in the manner heretofore described. Once the trigger 201 is released, the bell-crank lever 111 is free to pivot clockwise about the pivot pins 118, 119 from the solid line position to the phantom outline position of FIG. 1 which will pull the piston 166 upwardly relative to the cylinder 171. The clockwise pivoting of the bell-crank lever 111 is effected as the total effective forces of the springs 109, 131 and the now compressed spring 138 overcome the effective forces of the springs 103, 108 thereby resulting in clockwise rotation of the bell crank lever 111 from the solid toward the phantom outline position of FIG. 1. As the bell-crank lever 111 thus rotates clockwise pulling the piston 166 upwardly relative to the cylinder 171, the internal volume between the piston 166 and the cylinder 171 increases and automatically creates a negative pressure or vacuum which progressively increases as the piston 166 is progressively drawn upwardly out of the cylinder 171. As the piston 166 is moved upwardly, the cam 184 rises in the slot 196 from the solid line position in FIG. 3 and eventually its right-hand end contacts the edge 197 which rotates the cam 184 clockwise and lifts the locking ring 182 to its unlocked position (horizontal FIG. 3). When the locking ring 182 is unlocked, the spring 175 forcefully drives the hammer 180 downwardly to impact the end 190 against the large portion 293 (FIG. 7) of the ring-like portion 294 of the dermis-piercing member 295 with sufficient force to cause deflection thereof about the hinge means 298 to drive the pointed end 291 through the slit 277 of the portion 287 (FIG. 10) into the epidermis and slightly into the dermis of the skin Sk. This same deflection of the ring-like portion 294 carries the sleeve 300 downwardly to drive the wicking portion 287 of the wicking membrane 275 against the surface S of the indentation I of the skin Sk and blood flow caused by the pointed end 291 is augmented by the wicking nature of the membrane 275 and the vacuum created by the earlier described upward movement of the piston 166 which draws the blood from the area of the point 291 along the portion of the wicking membrane sandwiched between the test strip 285 and the medial wall 262 due to the position of the slots 280 and the cut-outs 278 at the end of the wicking membrane remote from the portion 287 thereof (FIG. 8). Thus, the blood is drawn from the area of the pointed end 291 along and through the wicking membrane 275 and impregnates the inactive surface 307 of the test strip 285. The construction of the test strip 285 is disclosed in the latter-noted application, the content of which is hereat incorporated by reference, but suffice it to say that the blood sample constituents which are to be tested migrate from the inactive surface 307 to the active surface 308 of the test strip 305. It should be particularly noted that the head 176 bottoms against the annular surface 179 slightly before the piston 166 has been lifted to its uppermost position outwardly of the cylinder 171. Therefore, during the last minor upward movement of the piston 166, the annular surface 179 thereof carries the head 176 upwardly and with it the hammer 180 which raises the end 190 from the position shown in FIG. 11 to the plane of the upper surface 256. The inherent resiliency of the material of the dermis-piercing member 295 now causes the inherent rebound of the ring-like portion 294 from the position shown in FIG. 11 to the original position (FIG. 9) which withdraws the pointed end 291 from the skin Sk virtually immediately after penetration. Thus, blood will immediate and freely flow from the pierced skin in sufficient quantity within approximately five seconds to wet/saturate the wicking membrane 285, even absent the negative pressure heretofore noted. If desired, the wicking membrane 285 might be provided with coagulant only adjacent the slots 280 to terminate the effect of the vacuum when blood from the pierced skin Sk has migrated/wicked through the wicking membrane 285 and reached the area of the slots 280.

After the blood sampling mechanism 10 has been held in the position shown in FIG. 3 for approximately five seconds after the point 291 had penetrated the skin Sk, the blood sampling mechanism is bodily lifted from the surface S.. The five seconds can be timed-out by an appropriate circuit of the testing, calibrating and discriminating testing mechanism 80 which after five seconds would sound a signal and/or light a light to indicate to the operator that the sampling is completed and the blood sampling mechanism 10 can be removed from the skin Sk.

When the blood sampling mechanism 10 is lifted from the skin Sk, the transfer arm 91 is now free to rotate from the position shown in FIG. 3 to the position shown in FIG. 1. The earlier described clockwise pivoting of the bell-crank lever 111, when the piston 166 moved up upon the release of the trigger 200, about the pivots 118, 119 from the solid to the phantom outline position of FIG. 1 carried the cable 102 across the dead center position defined by the axes of the pivots 118, 119 which is right-to-left movement in FIG. 1 to the phantom outline position of the cable 102. The latter movement of the bell crank lever 111 back to its phantom outline position loaded/augmented the force of the spring 108 in an upward direction. When the blood sampling mechanism 10 is now removed from the skin, the now greater force of the spring 108 draws the cable portion 106 upwardly against the now weaker force of the spring 109 causing the shaft 92 to rotate counterclockwise (FIG. 3) to rotate the transfer arm 91 counterclockwise from the blood sampling station 100 to the test pad loading and blood testing station 60. In the latter position, the "active" surface 308 of the test strip 305 of the test pad 50 faces the testing, calibrating and discriminating testing means 80 and the test results are read-out on an LED and/or a permanent strip print-out (not shown.)

During the clockwise pivoting of the bell crank lever 111 from the solid to the phantom outline position in FIG. 1, the spring 131 is also relaxed, upward force on the cable 130 is reduced, and the spring 38 moves the feed lever 61 from the position shown in FIG. 2 to the position shown in FIG. 1. Thereafter, as the door 18 is being closed, the cable 24 is retracted and wound in the groove 149 of the drum 143 by the torsion spring 146 which is permitted due to the one-way locking of the ratchet 150 relative to the ratchet wheel 151. The door 18 is then closed to cut-off power to the testing, calibrating and discriminating means 80. The test pad 50 may be retained on the arm 91 which will be dislodged by the next succeeding "fresh" test pad bottom-fed from the magazine 40 by the plunger 35 upon the subsequent opening of the door 18.

The structure heretofore described broadly also meets some specific relationships which occur automatically, particularly in regard to the operation of hammer 180 and the piston 166. For example, the velocity of the hammer 180 is two-to-three times the velocity of the piston 166 which assures that during the relative movement therebetween under the influence of the spring 175 after the trigger mechanism 200 has been released, the hammer 180 will, in fact, travel downwardly sufficiently to effect the application of force against the dermis-piercing member 295. This is augmented by hammer travel which is approximately one-quarter to one-third of the piston travel. Furthermore, during the downward travel of the piston 166 during its loading by the crank assembly mechanism 140, the shoulder 189 (FIG. 3) of the hammer 180 bottoms against the interior surface (unnumbered) of the end cap 191. When the latter occurs, the piston 166 continues to move downwardly before it is eventually locked by the operation of the trigger mechanism 200. This downward over travel of the piston 166 allows the piston 166 to rise approximately one and one-half times the thickness of the test pad 50 before the trigger mechanism 20 locks up which is turn assures that the hammer 180 will descend a sufficient distance to forcefully deflect the dermis-penetrating means 295, as shown in FIG. 10. Finally, the head 176 of the hammer 180 rests upon the annular surface 179 at a time when the piston 166 is one-tenth to one-twentieth of its stroke from the top position in order to raise the hammer 180 upwardly away from the position shown in FIG. 10 which allows the dermis-piercing member 295 to rebound under its inherent resilience which withdraws the point 291 from the skin to allow blood to freely flow against and through the wicking member 285.

Obviously, in keeping with the foregoing various modifications in the blood sampling mechanism 10 and the test pad 50 utilized therewith will be apparent to those skilled in the art. For example, since the test strip 305 is itself constructed from wicking material, the wicking membrane 285 can be totally eliminated and the surface 307 of the test strip 305 will be placed immediately against the surface 264 of the medial wall 262. The left-hand edge of the test strip 305, as viewed in FIG. 9 can be extended to the configuration of the wicking membrane portion 289 and might also be provided with a slit therein corresponding to the slit 277. However, since the test strip 305 is also constructed from rupturable material, the slit 277 is not a prerequisite and the pointed end 291 can as well be driven through an unslitted portion of the test strip 305, just as is possible in the case of the wicking membrane 285. Furthermore, since the wicking membrane 285 is eliminated, the test strip 305 can be positioned with the surfaces 307, 308 disposed respectively above and below each other, as viewed in FIG. 9, or opposite thereto, depending upon the relative position of the blood-testing means 80, and this alternate or upside position of the test strip 305 also permits the blood testing mechanism 80 to be positioned above or below the test pad 50 at the blood testing station 60. However, the latter might involve placing an opening through the wall 262 to permit either surface 307, 308 of the test strip 305 to be scanned from above or below, again as viewed in FIG. 9.

Though the blood sampling mechanism 10 has also been described in conjunction with the creation of negative pressure or a vacuum, it is to be understood that such is not necessarily required and a sufficient quantity of the blood will be drawn from the skin Sk by the wicking membrane 285 or directly by the test strip 305 in the absence of the wicking membrane 285. A sufficient quantity of blood is assured, particularly because the pointed end 291 of the dermis-piercing member 295 is virtually immediately withdrawn from the pierced skin Sk during the final retracting motion of the piston 166 heretofore described.

The wicking membrane 285 might also be provided with an appropriate agent adjacent the slots 280 to cause the material of the wicking membrane 285 to expand upon being contacted by the drawn blood which will "close" the slots 280 and/or lessen the "wicking" action of the wicking membrane 285 and thus serve as a vehicle for assuring repetitive accurate quantities of absorbed blood within the wicking membrane 285 and thus transfer therefrom to the test pad 305. Obviously, the same type of blood coagulant and/or expansion agent can be utilized in conjunction with the test strip 305 when the wicking membrane 285 is not part of the overall test pad 50.

Through considered apparent from the description heretofore, the calibration markings which can be applied to the magazine 40 are preferably applied immediately adjacent the calibration and blood testing means 80 so as to be sensed thereby, and one such calibration code M is illustrated in FIG. 1. In such cases in which the seal 44 might not be provided with an appropriate calibration code the calibration code M would be applied to the magazine 40 and, upon the opening of the door 18 the calibration circuitry (not shown) of the calibration and blood testing means 80 would read the calibration code M to appropriately condition the blood testing circuitry (not shown) of the means 80 for subsequent accurate blood testing and information read-out. If the calibration code M is placed upon the seal 44, the same might necessarily have to be scanned from below when the portion of the seal 44 has been transferred with the lowermost test pad 50 LTP upon the transfer arm 91. However, the calibration code M can as well be placed upon the surface 257 (FIG. 8) of the test pad 50 which is, as heretofore described, the surface presented toward the discriminating, calibrating and blood testing mechanism 80 when the test pad 50 is initially inserted into the grooves 95, 96 of the transfer arm 91. Thus, with the code M placed upon the surface 257, the optics or equivalent detection/sensing mechanism of the means 80 is directed downwardly in FIG. 1 for initial sensing and appropriate calibration of the blood sample testing circuitry thereof. Obviously, only the lowermost test pad 50 LTP of each magazine 40 need be provided with the code M and, as was heretofore noted, this test pad would be discharged if a portion of the seal 44 were carried thereby, but if the seal 44 was manually removed prior to securing the magazine 40 to the magazine support 26, even the lowermost test pad 50 LTP can be used for blood sampling and testing purposes once, of course, the mechanism 80 has been appropriately calibrated through the code M.

While the characteristics of the test strip 305 are incorporated hereat by reference from the latter-identified patent application, it should be noted that the test strip 305 may be utilized to measure virtually any property of the blood sample with or without the utilization of the wicking membrane 285. The test pad 305 is simply treated with a measured amount of one or more chemicals and/or enzymes which will react with blood glucose to predictably change one or more properties of the blood sample. For example, the enzyme glucose oxidase may be used to catalyse a reaction to produce gluconic acid and hydrogen peroxide, and a predictable color change dependent on the level of glucose in the measured sample, but also dependent on many other factors such as rate of reaction, temperature, time and the amount of blood in the sample. However, all of the latter factors are capable of control and measurement by conventional circuitry of the discriminating, calibrating and testing mechanism 80 and the electronic circuitry thereof. Both the temperature and the rate of temperature change can, for example, be sense due to the heat of the reaction as a measure of blood glucose. The latter is readily accomplished since resistance thermometers can measure temperature changes in the order of 0.005° C., and electronic timing has similar accuracy.

The sleeve 300 can also be eliminated, though the use thereof is preferably since the sleeve 300 performs two beneficial functions during blood testing (FIG. 10), namely, the circular lip 301 thereof assures that the portion 289 of the wicking member 285 is placed relatively uniformily and flat against the surface S of the skin Sk in the area of the indentation I (FIG. 10), and the sleeve 300 also creates pressure internal of the dermis to force blood out through the pierced opening of the skin Sk upon the retraction of the pointed end 291. Obviously, the creation of internal forces urging the blood out of the pierced opening of the skin Sk assures adequate blood flow and a suitable quantity of blood within the preferable 2-5 second range that the blood sampling mechanism 10 will be held upon the skin Sk after pointed end penetration.

The relatively nonintrusive nature of the pointed end 291 is characterized primarily by the extremely short and thin nature of the pointed end 291 of the dermis-piercing member 295. As a reference, a conventional lancet is approximately 0.030 inch (0.76 mm) in diameter and the pointed end thereof tapers from this diameter to a point which effects skin penetration of 0.090 inch (2.29 mm). However, the pointed end 291 is approximately 0.007 inch (0.18 mm) wide, 0.003 inch (0.08 mm) thick, and the depth of penetration into the skin from the surface S (FIG. 10) inward is only 0.007 inch (0.018 mm). The latter comparison readily accentuates the nonintrusive nature of the present dermis-piercing member which, as heretofore noted, lessens pain, physical and emotional, prevents ingress of contaminants of the pierced epidermis and at the same time assures adequate blood flow.

Although a preferred embodiment of the invention has been specifically illustrated and described herein, it is to be understood that minor variations may be made in the apparatus without departing from the spirit and scope of the invention, as defined in the appended claims.

We claim:

1. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying said test pad from said blood sampling station after the blood sample has been obtained to said blood testing station.

2. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station.

3. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, and means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station along a first path of travel in a first direction and returning the test pad after the blood sample has been obtained back to said blood testing station generally along said first path of travel but in a second direction generally opposite said first direction.

4. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, and means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally arcuate path of travel.

5. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally reciprocal path of travel.

6. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally reciprocal arcuate path of travel.

7. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood testing station at which said blood sample testing means is located, means for locating a fresh test pad at said blood testing station, and means for conveying a fresh test pad from said blood testing station to said blood sampling station and returning the test pad after the blood sample has been obtained back to said blood testing station for subsequent testing by said blood sample testing means.

8. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, means for defining a blood testing station at which said blood sample testing means is located, a magazine adapted to house a plurality of fresh test pads each having a dermis-piercing member and a pointed end, means for sequentially feeding fresh test pads individually from said magazine to said blood testing station, and means for conveying each fresh test pad from said blood testing station to said blood sampling station and returning the test pad after the blood sample has been obtained back to said blood testing station for subsequent testing by said blood sample testing means.

9. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for supplying a force to said dermis-piercing member in a direction to move said pointed end beyond one of said opposite surfaces to pierce the dermis and thereby obtain a blood sample, means for testing the blood sample, means for defining a blood sampling station at which the blood sample is obtained, means for locating said test pad at said blood sampling station with the dermis-piercing member pointed end projecting in a predetermined direction, said force applying means being located at said blood sampling station contiguous said piercing member pointed end, and said force applying means imparting a force to move said piercing member to move said pointed end in said predetermined direction.

10. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, said test pad includes a test strip, means for wicking blood away from the area of the dermis-piercing member pointed end to the test strip, and means for creating negative pressure so as to augment blood flow through the wicking means toward said test strip.

11. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, said test pad includes a test strip, means for wicking blood away from the area of the dermis-piercing member pointed end to the test strip, and said blood wicking means being a strip of wicking material contiguous said test strip and being adapted to contact the area of the dermis pierced by said piercing member pointed end.

12. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, said test pad includes a test strip, means for wicking blood away from the area of the dermis-piercing member pointed end to the test strip, said blood wicking means being a strip of wicking material contiguous said test strip and being adapted to contact the are of the dermis pierced by said piercing member pointed end, and means for creating negative pressure so as to augment blood flow through the wicking strip toward said test strip.

13. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing the blood sample, resilient means for carrying said pointed end during movement thereof between home and dermis-piercing positions thereof, means for defining a blood sampling station at which the blood sample is obtained, means for defining a blood testing station at which the blood sample is tested by said blood sample testing means, means for locating said test pad at said blood testing station with said pointed end projecting in a first predetermined direction, and means for conveying said test pad from said blood testing station to said blood sampling station with said pointed end projecting in a second predetermined second direction opposite to said first predetermined direction.

14. A blood sampling mechanism comprising a test pad of a predetermined thickness set-off between opposite relatively closely spaced surfaces imparting a thin configuration to said test pad, said test pad carrying a dermis-piercing member having a pointed end, said pointed end being disposed inboard of said opposite surfaces, means for applying a force to said dermis-piercing member in a direction to move said pointed end beyond one of said opposite surfaces to pierce the dermis and thereby obtain a blood sample, means for testing blood sample, a rupturable wicking membrane in contiguous spanning relation ship to said pointed end and in generally transverse relationship to said predetermined direction, and said force applying means applies a force of sufficient magnitude to said dermis-piercing member to pierce said rupturable membrane incident to piercing the dermis.

15. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for defining a blood testing station at which the blood sample is tested by said blood sample testing means, and means for conveying said test pad from said blood sampling station after the blood sample has been obtained to said blood testing station.

16. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station.

17. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station along a first path of travel in a first direction and returning the test pad after the blood sample has been obtained back to said blood testing station generally along said first path of travel but in a second direction generally opposite said first direction.

18. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said firs position under the inherent resiliency thereof, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally arcuate path of travel.

19. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally reciprocal path of travel.

20. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally reciprocal arcuate path of travel.

21. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood testing station at which said blood sample testing means is located, means for locating a fresh test pad at said blood testing station, and means for conveying a fresh test pad from said blood testing station to said blood sampling station and returning the test pad after the blood sample has been obtained back to said blood testing station for subsequent testing by said blood sample testing means.

22. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood testing station at which said blood sample testing means is located, a magazine adapted to house a plurality of fresh test pads each having a dermis-piercing member and a pointed end, means for sequentially feeding fresh test pads individually from said magazine to said blood testing station, and means for conveying each fresh test pad from said blood testing station to said blood sampling station and returning the test pad after the blood sample has been obtained back to said blood testing station for subsequent testing by said blood sample testing means.

23. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, means for defining a blood sampling station at which the blood sample is obtained, means for locating said test pad at said blood sampling station with the dermis-piercing member pointed end projecting in a predetermined direction, said force applying means being located at said blood sampling station contiguous said piercing member pointed end, and said force applying means imparting a force to move said piercing member to move said pointed end in said predetermined direction.

24. A blood sampling mechanism comprising a substantially thin and flat test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end at least partially through said test pad to pierce the dermis and thereby obtain a blood sample, said resilient dermis-piercing member being returnable from said second position to said first position under the inherent resiliency thereof, means for testing the blood sample, said test pad includes a test strip, and means for wicking blood away from the area of the dermis piercing member pointed end to the test strip.

25. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, said test pad includes a test strip, means for wicking blood away from the area of the dermis-piercing member pointed end to the test strip, and means for creating negative pressure so as to augment blood flow through the wicking means toward said test strip.

26. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, said test pad includes a test strip, means for wicking blood away from the area of the dermis-piercing member pointed end to the test strip, and said blood wicking means being a strip of wicking material contiguous said test strip being adapted to contact the area of the dermis pierced by said piercing member pointed end.

27. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, said test pad includes a test strip, means for wicking blood away from the area of the dermis-piercing member pointed end to the test strip, said blood wicking means being a strip of wicking material contiguous said test strip and being adapted to contact the area of the dermis pierced by said piercing member pointed end, and means for creating negative pressure so as to augment blood flow through the wicking strip toward said test strip.

28. A blood sampling mechanism comprising a test pad, said test pad carrying a resilient dermis-piercing member having a pointed end, said dermis-piercing member being deflectable from a first inoperative position to a second operative dermis-piercing position, means for deflecting said dermis-piercing member from said first position to said second position to move said pointed end to pierce the dermis and thereby obtain a blood sample, said resilient dermis-piercing member being returnable from said second position to said first position under the inherent resiliency thereof, means for testing the blood sample, said dermis-piercing member pointed end projects in a predetermined direction, a wicking membrane concealing said dermis piercing member pointed end, and said force applying means creates a force of sufficient magnitude to cause said pointed end to pierce through said membrane incident to piercing the dermis.

29. A blood sampling mechanism comprising a test pad, said test pad carrying a dermis-piercing member having a pointed end, said dermis-piercing member pointed end projecting in a predetermined direction, a rupturable wicking membrane in contiguous spanning relationship to said pointed end and in generally transverse relationship to said predetermined direction, means for applying a force to said dermis-piercing member to move said pointed end in said predetermined direction to pierce said rupturable wicking membrane and pierce the dermis thereby obtaining a blood sample, and means for testing the blood sample.

30. The blood sampling mechanism as defined in claim 29 including means for evacuating blood away from the area of the dermis-piercing member pointed end.

31. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining blood sampling station at which the blood sample is obtained, means for defining a blood testing station at which the blood sample is tested by said blood sample testing means, and means for conveying said test pad from said blood sampling station after the blood sample has been obtained to said blood testing station.

32. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station.

33. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for test the blood sample, means for defining a blood sampling station at which the blood sample is obtained, means for defining a blood testing station at which the blood sample is tested by said blood sample testing means, and means for conveying a fresh test pad from said blood testing station to said blood sampling station along a first path of travel in a first direction and returning the test pad after the blood sample has been obtained back to said blood testing station generally along said first path of travel but in a second direction generally opposite said first direction.

34. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally arcuate path of travel.

35. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood sampling station at which the blood sample is obtained, means for defining a blood testing station at which the blood sample is tested by said blood sample testing means, and means for conveying a fresh test pad from said blood testing station to said blood sampling station and returning the test pad after the blood sample has been obtained back to said blood testing station along a generally reciprocal path of travel.

36. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood sampling station at which the blood sample is obtained, means for defining a blood test station at which the blood sample is tested by said blood sample testing means, and means for conveying a fresh test pad from said blood testing station to said blood sampling station and returning the test pad after the blood sample has been obtained back to said blood testing station along a generally reciprocal arcuate path of travel.

37. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood testing station at which said blood sample testing means is located, means for locating a fresh test pad from said blood testing station; and means for conveying a fresh test pad from said blood testing station to said blood sampling station and returning the test pad after the blood sample has been obtained back to said blood testing station for subsequent testing by said blood sample testing means.

38. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood testing station at which said blood sample testing means is located, a magazine adapted to house a plurality of fresh test pads each having a dermis-piercing member and a pointed end, means for sequentially feeding fresh test pads individually from said magazine to said blood testing station, and means for conveying each fresh test pad from said blood testing station to said blood sampling station and returning the test pad after the blood sample has been obtained back to said blood testing station for subsequent testing by said blood sample testing means.

39. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, means for defining a blood sampling station at which the blood sample is obtained, means for locating said test pad at said blood sampling station with the dermis-piercing member pointed end projecting in a predetermined direction, said force applying means being located at said blood sampling station contiguous said piercing member pointed end, and said force applying means imparting a force to move said piercing member to move said pointed end in said predetermined direction.

40. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, resilient means for carrying said pointed end during movement thereof between home and dermis-piercing positions thereof, means for defining a blood sampling station at which the blood sample is obtained, means for defining a blood testing station at which the blood sample is tested by said blood sample testing means, means for locating said test pad at said blood testing station with said pointed end projecting in a first predetermined direction, and means for conveying said test pad from said blood testing station to said blood sampling station with said pointed end projecting in a second predetermined second direction opposite to said first predetermined direction.

41. A blood sampling mechanism comprising a test pad, said test pad carrying a dermis-piercing member having a pointed end, said dermis-piercing member pointed end projecting in a predetermined direction, a rupturable wicking membrane in contiguous spanning relationship to said pointed end and in generally transverse relationship to said predetermined direction, means for applying a force to said dermis-piercing member to move said pointed end in said predetermined direction to pierce said rupturable wicking membrane and pierce the dermis thereby obtaining a blood sample, means for testing the blood sample, said dermis-piercing member is resilient and deflectable from a first inoperative position to a second operative dermis piercing position, said force applying means is effective to deflect said resilient piercing member from said first position to said second position to move said pointed end and thereby obtain a blood sample, and said resilient dermis-piercing member being returnable from said second position to said first position under the inherent resiliency thereof.

42. A blood sampling mechanism comprising a test pad, said test pad carrying a dermis-piercing member having a pointed end, said dermis-piercing member pointed end projecting in a predetermined direction, a rupturable wicking membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, and said rupturable membrane includes means for wicking blood away from the area of the dermis-piercing member pointed end.

43. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, said test pad includes a test strip contiguous said rupturable membrane, and said rupturable membrane includes means for wicking blood away from the area of the dermis-piercing member pointed end to said test strip.

44. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, said test pad includes a test strip contiguous said rupturable membrane, said rupturable membrane includes means for wicking blood away from the area of the dermis-piercing member pointed end to said test strip, and means for creating negative pressure so as to augment blood flow through said wicking means toward said test strip.

45. A blood sampling mechanism comprising a test pad, said test pad carrying a dermis-piercing member having a pointed end, said dermis-piercing member pointed end projecting in a predetermined direction, a rupturable membrane in contiguous spanning relationship to said pointed end and in generally transverse relationship to said predetermined direction, means for applying a force to said dermis-piercing member to move said pointed end in said predetermined direction to pierce said rupturable membrane and pierce the dermis thereby obtaining a blood sample, means for testing the blood sample, said rupturable membrane is formed of blood wicking material, said dermis-piercing member is resilient and deflect able from a first inoperative position to a second operative dermis-piercing position, said force applying means is effective to deflect said resilient piercing member from said first position to said second position to move said pointed end and thereby obtain a blood sample, and said resilient dermis-piercing member being returnable from said second position to said first position under the inherent resiliency thereof.

46. A blood sampling mechanism comprising means for defining a blood sampling station, means for defining a blood test pad loading and testing station, said test pad loading and testing station carrying a dermis-piercing member having a pointed end, means for locating a fresh test pad at said blood test pad loading and testing station with said pointed end projecting in a first predetermined direction, means for transferring the fresh blood test pad from the loading and testing station to the blood sampling station with said pointed end at said blood sampling station projecting in a second predetermined direction differing from said first predetermined direction, means at said blood sampling station to move said dermis-piercing member to pierce the dermis by said pointed end thereby obtaining a blood sample, said transferring means being operative for transferring the blood sampled test pad to said blood test pad loading and testing station, and means at said blood test pad loading and testing station for testing the blood sample of the blood sampled test pad thereat.

47. The blood sampling mechanism as defined in claim 46 wherein said transferring means is effected to position said test pad at said stations with said first and second predetermined directions being oppositely directed.

48. The blood sampling mechanism as defined in claim 46 wherein said blood sample testing means is located contiguous said pointed end in said first predetermined direction.

49. The blood sampling mechanism as defined in claim 46 wherein said transferring means defines a generally curved reciprocal path of travel between said stations.

50. The blood sampling mechanism as defined in claim 46 wherein said test pad includes a blood wicking membrane, and said dermis-piercing member moving means is effective to pierce through said blood wicking membrane at said blood sampling station incident to obtaining a blood sample.

51. The blood sampling mechanism as defined in claim 46 wherein said test pad includes a test strip and a blood wicking strip with adjacent opposing surfaces thereof being in contact, said dermis-piercing member moving means is effective to pierce through said blood wicking strip at said blood sampling station incident to obtaining a blood sample which is wicked by said wicking strip to said opposing test strip surface, and said transferring means is effective to position said test pad at said test pad loading and testing station with a surface opposite said test strip opposing surface facing said blood sample testing means.

52. A blood test pad comprising a body of a predetermined thickness set-off between opposite relatively closely spaced surfaces imparting a generally thin and flat configuration to said test pad body, said test pad body including a resilient dermis-piercing member having a pointed end, said pointed end being deposed inboard of said opposite surfaces, said dermis-piercing member being constructed and arranged for effecting movement of said piercing member in a direction to move said pointed end beyond one of said opposite surfaces incident to piercing the dermis and obtaining a blood sample, said pointed end projects in a predetermined direction, and a rupturable wicking membrane in contiguous spanning relationship to said pointed end and in generally transverse relationship to said predetermined direction which is adapted to be pierced through by said pointed end during movement thereof beyond said one surface.

53. The blood test pad as defined in claim 52 wherein said pointed end projects in a predetermined direction, and a rupturable membrane in contiguous spanning relationship to said pointed end and in generally transverse relationship to said predetermined direction which is adapted to be pierced through by said pointed end during movement thereof beyond said one surface.

54. A blood test pad comprising a body of a predetermined thickness set-off between opposite relatively closely spaced surfaces imparting a generally thin configuration to said test pad body, said test pad body including a dermis-piercing member having a pointed end, said pointed end being deposed inboard of said opposite surfaces, said dermis-piercing member being constructed and arranged for effecting movement of said piercing member in a direction to move said pointed end beyond one of said opposite surfaces incident to piercing the dermis and obtaining a blood sample, said pointed end projects in a predetermined direction, and a rupturable wicking membrane in contiguous spanning relationship to said pointed end and in generally transverse relationship to said predetermined direction which is adapted to be pierced through by said pointed end during movement thereof beyond said one surface.

55. A blood test pad comprising a body of a predetermined thickness set-off between opposite relatively closely spaced surfaces imparting a generally thin configuration to said test pad body, said test pad body including a dermis-piercing member having a pointed end, said pointed end being deposed inboard of said opposite surfaces, said dermis-piercing member being constructed and arranged for effecting movement of said piercing member in a direction to move said pointed end beyond one of said opposite surfaces incident to piercing the dermis and obtaining a blood sample, said pointed end projects in a predetermined direction, a test strip and a wicking strip each having opposite surfaces, a first surface of each of said strips being in contact with each other, and said wicking strip being in contiguous spanning relationship to said pointed end and in generally transverse relationship to said predetermined direction thereby being adapted to be pierced through by said pointed end during movement thereof beyond said one surface.

56. A blood test pad comprising a body of a predetermined thickness set-off between opposite relatively closely spaced surfaces imparting a generally thin configuration to said test pad body, said test pad body including a dermis-piercing member having a pointed end, said pointed end being deposed inboard of said opposite surfaces, said dermis-piercing member being constructed and arranged for effecting movement of said piercing member in a direction to move said pointed end beyond one of said opposite surfaces incident to piercing the dermis and obtaining a blood sample, said dermis-piercing member is constructed from resilient deflectable material, said pointed end projects in a predetermined direction, and a rupturable wicking membrane in contiguous spanning relationship to said pointed end and in generally transverse relationship to said predetermined direction which is adapted to be pierced through by said pointed end during movement thereof beyond said one surface.

57. A blood test pad comprising a body of a predetermined thickness set-off between opposite relatively closely spaced surfaces imparting a generally thin configuration to said test pad body, said test pad body including a dermis-piercing member having a pointed end, said pointed end being deposed inboard of said opposite surfaces, said dermis-piercing member being constructed and arranged for effecting movement of said piercing member in a direction to move said pointed end beyond one of said opposite surfaces incident to piercing the dermis and obtaining a blood sample, said dermis-piercing member is constructed from resilient deflectable material, said pointed end projects in a predetermined direction, a test strip and a wicking strip each having opposite surfaces, a first surface of each of said strips being in contact with each other, and said wicking strip being in contiguous spanning relationship to said pointed end and in generally transverse relationship to said predetermined direction thereby being adapted to be pierced through by said pointed end during movement thereof beyond said one surface.

58. A blood test pad comprising a test pad, said test pad including a wicking membrane and carrying a resilient dermis-piercing member having a pointed end, said dermis-piercing member being constructed and arranged for deflection under external force from a first inoperative position to a second operative dermis-piercing position in which said pointed end projects through said wicking membrane and return from said second position to said first position under the inherent resiliency thereof upon removal of the external force.

59. The blood test pad as defined in claim 58 including hinge means remote from said pointed end for effecting said deflection and return.

60. A blood test pad comprising a test pad, said test pad carrying a resilient dermis-piercing member having a pointed end, said dermis-piercing member being constructed and arranged for deflection under external force from a first inoperative position to a second operative dermis-piercing position and return from said second position to said first position under the inherent resiliency thereof upon removal of the external force, said pointed end projects in a predetermined direction, and a rupturable wicking membrane in contiguous spanning relationship to said pointed end and in generally transverse relationship to said predetermined direction which is adapted to be pierced through by said pointed end during movement thereof to the second position.

61. A blood test pad comprising a test pad, said test pad carrying a resilient dermis-piercing member having a pointed end, said dermis-piercing member being constructed and arranged for deflection under external force from a first inoperative position to a second operative dermis-piercing position and return from said second position to said first position under the inherent resiliency thereof upon removal of the external force, said pointed end projects in a predetermined direction, a test strip and a wicking strip each having opposite surfaces, a first surface of each of said strips being in contact with each other, and said wicking strip being in contiguous spanning relationship to said pointed end and in generally transverse relationship to said predetermined direction thereby being adapted to be pierced through by said pointed end during movement thereof to the second position.

62. A blood test pad comprising a dermis-piercing member having a pointed end, said dermis-piercing member pointed end projecting in a predetermined direction, a rupturable porous membrane in contiguous spanning relationship to said pointed end and in generally transverse relationship to said predetermined direction, and means for effecting movement of said piercing member in a direction to move said pointed end through said rupturable porous membrane incident to obtaining a blood sample.

63. A blood test pad comprising a dermis-piercing member having a pointed end, said dermis-piercing membrane pointed end projecting in a predetermined direction, a rupturable membrane in contiguous spanning relationship to said pointed end and in generally transverse relationship to said predetermined direction, means for effecting movement of said piercing member in a direction to move said pointed end through said rupturable membrane incident to obtaining a blood sample, said rupturable membrane includes wicking material.

64. A blood test pad comprising a dermis-piercing member having a pointed end, said dermis-piercing membrane pointed end projecting in a predetermined direction, a rupturable membrane in contiguous spanning relationship to said pointed end and in generally transverse relationship to said predetermined direction, means for effecting movement of said piercing member in a direction to move said pointed end through said rupturable membrane incident to obtaining a blood sample, a test strip, said rupturable membrane and test strip each having opposite surfaces, and a first surface of each of said test strip and rupturable membrane being in contact with each other.

65. A blood test pad as defined in claim 64 wherein said rupturable membrane includes wicking material.

66. The blood test pad as defined in claim 65 wherein said rupturable membrane includes wicking material.

67. The blood test pad as defined in claim 64 wherein said rupturable membrane includes wicking material.

68. A blood test pad comprising a body of a predetermined thickness set-off between opposite relatively closely spaced surfaces imparting a generally thin configuration to said test pad body, said test pad body including a dermis-piercing member having a pointed end, said pointed end being disposed inboard of said opposite surfaces, said dermis-piercing member being constructed and arranged for effecting movement of said piercing member in a direction to move said pointed end beyond one of said opposite surfaces incident to piercing the dermis and obtaining a blood sample, means contiguous said pointed end for collecting a sample of blood upon said pointed end effecting dermis-piercing, said blood sample collecting means includes blood reacting chemistry agents, said blood sample collecting means is a blood sample test strip, and a wicking membrane having a portion disposed inboard relative to said test strip.

69. The blood test pad as defined in claim 68 wherein a portion of said wicking membrane is in overlying spanning relationship to said pointed end.

70. A blood test pad comprising a body of a predetermined thickness set-off between opposite relatively closely spaced surfaces imparting a generally thin configuration to said test pad body, said test pad body including a dermis-piercing member having a pointed end, said pointed end being disposed inboard of said opposite surfaces, said dermis-piercing member being constructed and arranged for effecting movement of said piercing member in a direction to move said pointed end beyond one of said opposite surfaces incident to piercing the dermis and obtaining a blood sample, means contiguous said pointed end for collecting a sample of blood upon said pointed end effecting dermis-piercing, said blood sample collecting means includes blood reacting chemistry agents, said blood sample collecting means is a blood sample test strip in spanning relationship to said pointed end, and a slit in said test strip aligned with said dermis-piercing member pointed end.

* * * * *